(12) United States Patent
Tseng (10) Patent No.: US 7,633,404 B2
(45) Date of Patent: Dec. 15, 2009

(54) MEASUREMENT INDICATION METHOD AND APPARATUS THEREOF

(75) Inventor: Daniel C. M. Tseng, Taipei County (TW)

(73) Assignee: K-Jump Health Co., Ltd., Taipei County (TW)

(*) Notice: Subject to any disclaimer, the term of this patent is extended or adjusted under 35 U.S.C. 154(b) by 373 days.

(21) Appl. No.: 11/819,459

(22) Filed: Jun. 27, 2007

(65) Prior Publication Data

US 2009/0002138 A1 Jan. 1, 2009

(51) Int. Cl.
*G08B 5/00* (2006.01)
*G09G 3/04* (2006.01)
*A61B 5/00* (2006.01)

(52) U.S. Cl. .............. 340/815.4; 340/815.44; 340/815.65; 340/815.43; 340/525; 340/462; 340/691.1; 340/691.6; 340/331; 600/300; 345/35; 345/40; 73/901; 374/100

(58) Field of Classification Search .............. 340/815.4, 340/815.44, 815.65; 345/35, 40
See application file for complete search history.

(56) References Cited

U.S. PATENT DOCUMENTS 4,570,226 A * 2/1986 Aussedat .................... 701/123

5,486,914 A * 1/1996 Denove et al. .............. 356/221
6,329,926 B1 * 12/2001 Hollander et al. ...... 340/815.45
6,674,416 B2 * 1/2004 Kamei et al. .................. 345/39

FOREIGN PATENT DOCUMENTS

TW    M284356 U    1/2006
TW    M284890 U    1/2006

* cited by examiner

*Primary Examiner*—Donnie L Crosland
(74) *Attorney, Agent, or Firm*—Muncy, Geissler, Olds & Lowe, PLLC (57) ABSTRACT

A measurement indication method and an apparatus to indicate difference between a measured result taken by a medical measurement instrument and a normal digital value according to medical theory. The medical measurement instrument includes at least a measurement element, a power supply, at least one processing unit and the apparatus to implement the measurement indication method. The apparatus includes a plurality of indication lamps capable of emitting light of three or more colors. The number and lighting color of the indication lamps can be changed sequentially according to the difference of the measured digital value and a normal digital value range. Thereby users can easily determine the difference between the measured result and the normal value. And the measured value can be indicated in graphics.

18 Claims, 7 Drawing Sheets

| Temperature (°C) | Color (R/Y/G) | Lamp 1 | 2 | 3 | 4 | 5 |
|---|---|---|---|---|---|---|
| ≤ 35.6 | Y | ■ | ■ | ■ | ■ | ■ |
| 35.7 | Y | ■ | ■ | ■ | ■ | |
| 35.8 | Y | ■ | ■ | ■ | | |
| 35.9 | Y | ■ | ■ | | | |
| 36.0 | Y | ■ | | | | |
| 36.1 | G | ■ | | | | |
| 36.2 | G | ■ | ■ | | | |
| 36.3 | G | ■ | ■ | ■ | | |
| 36.4 | G | ■ | ■ | ■ | ■ | |
| 36.5 | G | ■ | ■ | ■ | ■ | ■ |
| 36.6 | G | ■ | ■ | ■ | ■ | |
| 36.7 | G | ■ | ■ | ■ | | |
| 36.8 | G | ■ | ■ | | | |
| 36.9 | G | ■ | | | | |
| 37.0 | Y | ■ | | | | |
| 37.1 | Y | ■ | ■ | | | |
| 37.2 | Y | ■ | ■ | ■ | | |
| 37.3 | Y | ■ | ■ | ■ | ■ | |
| 37.4 | Y | ■ | ■ | ■ | ■ | ■ |
| 37.5 | R | ■ | | | | |
| 37.6 | R | ■ | ■ | | | |
| 37.7 | R | ■ | ■ | ■ | | |
| 37.8 | R | ■ | ■ | ■ | ■ | |
| ≥ 37.8 | R | ■ | ■ | ■ | ■ | ■ |

MEASUREMENT INDICATION METHOD AND APPARATUS THEREOF

FIELD OF THE INVENTION

The present invention relates to a measurement indication method and an apparatus thereof and particularly to a method and a display device that provide medical measurement digital values for reference through number and color of lighting lamps.

BACKGROUND OF THE INVENTION

Medical science advances constantly and health care is an issue most people deem seriously. These days many simple medical measurement instruments such as thermometers, blood pressure meters, fat detection meters and the like are available for people to use themselves. For people to accurately know their own health conditions, aside from knowing how to correctly use the medical measurement instruments, they also have to understand how to correctly judge the measured outcome. The conventional medical measurement instruments, such as R.O.C. patent No. M284356, entitled "Blood pressure meter" indicates merely the measurement result by a digital value through a LCD device. The digital value alone does not inform users whether it is in the normal range. The digital value has to be used in cooperation with other measurement units (such as mmHg for measuring the blood pressure) to become meaningful. Hence to understand a person's physical condition the person has to know the correct measurement method and interpret the measured value. For people who do not have fundamental medical knowledge interpreting the measured value could be baffling, or mistaken interpretation could occur. After people have known how to interpret the measured digital value, they also have to know the normal range of the digital value to understand their physical conditions. People generally have a faster understanding and response to graphics and colors. Different colors give the brain different stimulations to allow people to generate different alerts (such as red color has the longest wavelength and is processed by the brain at a higher priority, thus gives people an alert sense). Hence the perception speed and degree of the brain on a measured digital value is slower and lower than color alteration and intensity variation of lighting lamps. Moreover, displaying merely the measured digital value does not generate instant alert to people who do not have sufficient medical knowledge or perception. Hence there is still room for improvement on the presentation method of the conventional medical measurement instruments in terms of enabling people of no medical knowledge or insufficient perception to quickly understand their physical conditions. This phenomenon of lacking graphic presentation also happens to the measurement of the physiological conditions of other living things (such as measuring the heart beat of cats). It also begs for improvement. R.O.C. patent No. M284890, entitled "Improved digital thermometer" discloses a technique which can generate two colors through a backlight panel to indicate a measured result. It indicates by mixing two colors of light in different ratio of light intensity. As people differ in their sensitivity and perception on colors, they have difficulty to differentiate the measurement variation by seeing the color mixed in varying ratios (such as to differentiate 60% of green light and 40% of red light). The interpretation result of different people could be different. Hence an improvement still is required to simplify the interpretation of measured result.

SUMMARY OF THE INVENTION

In view of the conventional medical measurement instruments which indicate only measured digital values without providing easy to understand reference information and unable to allow users who do not have medical knowledge to instantly know their health conditions, the primary object of the present invention is to provide a method to compare measured digital values with theoretical normal digital values and present the compared result in graphics through lighting lamps and also provide a display device to make the measured result easy to understand.

The measurement indication method and apparatus thereof of the invention aim to indicate the difference of a result measured by a medical measurement instrument and a normal digital value according to medical theory. The medical measurement instrument includes at least a measurement element, a power supply, at least one processing unit and a measurement display device, and also may include a user interface, a digital display device and a buzzer alarm. The measurement element aims to measure physiological conditions of living things and send electronic signals to the processing unit. The processing unit issues signals to the digital display device. The buzzer alarm and the digital display device indicate measured result. The digital display device has a plurality indication lamps to generate three or more colored lights. The number and colors of the indication lamps vary according to the difference of the measured digital value and a normal digital value range. Thereby users can easily determine the difference between the measured result and the normal digital value. And the measured digital value can be presented in graphics.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
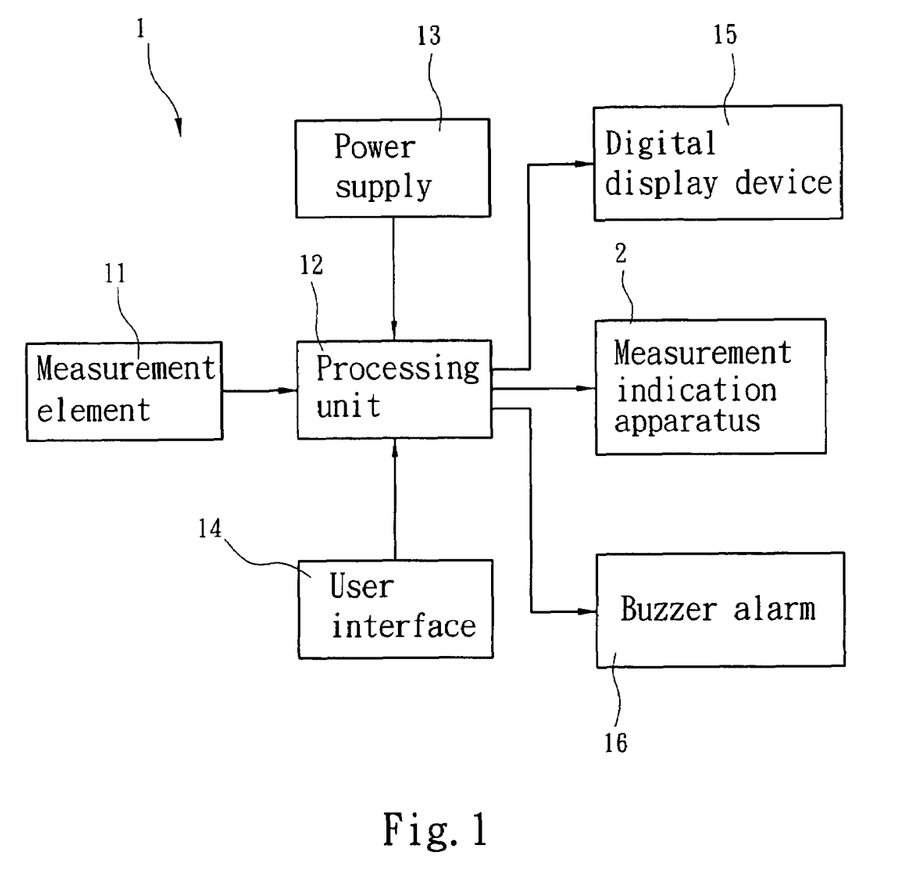
FIG. 1 is a block diagram of the structure of the invention.

The present invention provides a measurement indication method and an apparatus for implementing the method. The method includes setting a base segment and a plurality of digital value segments at an equal interval; measuring a living thing to get a measured digital value; and controlling a plurality of indication lamps that have three or more colors to indicate relative difference between the measured result that shows the condition of the living thing and a theoretical digital value. The method, first, sets an initial condition by lighting all the indication lamps in a first indication color, and determining a digital value segment which covers the measured digital value; calculates the segment number between the measured digital value segment and the base segment; turns off sequentially the indication lamps of the first color according to the segment number between the measured digital value segment and the base segment until only one set of indication lamp is lighting; in the event that the number of the indication lamps of the first indication color being turned off does not reach the segment number between the measured digital value segment and the base segment, the indication lamps are turned on sequentially to emit light of a second indication color; in the event that the number of the indication lamps being turned on for the second indication color still does not reach the segment number between the measured digital value segment and the base segment, the color light of the indication lamps is changed to a third indication color, and the indication lamps are turned on sequentially to emit the light of the third indication color increasing in number to represent the segment number between the measured digital value segment and the base segment; in the event that the indication lamps can emit light of more than three colors, change of the color continues and repeats the increasing from the beginning until they can represent the segment number between the measured digital value segment and the base segment. Please refer to FIG. 1 for the structural block diagram of an embodiment of the invention. The measurement indication apparatus 2 according to the invention aims to indicate the difference of a measured result of a medical measurement instrument 1 and a normal digital value according to medical theory. The medical measurement instrument 1 includes at least a measurement element 11, a power supply 13, at least one processing unit 12 and the measurement indication apparatus 2, and also may include a user interface 14, a digital display device 15 and a buzzer alarm 16. The medical measurement instrument 1 may be a thermometer, a blood pressure meter, a weight meter or a composite measurement instrument for measuring multiple functions, and has one or more measurement element 11 to measure the physiological conditions of living things in electronic signals and send the electronic signals to the processing unit 12. The processing unit 12 issues signals to the digital display device 15, buzzer alarm 16 and measurement indication apparatus 2 to indicate the measured result. The measurement indication apparatus 2 has a lamp set consisting of a plurality of indication lamps (referring to FIG. 2) to emit three or more colored lights. According to the difference of the measured value and a normal digital value range the number and color of the indication lamps are turned on and changed sequentially to represent the measured digital value in graphics.

Figure 2:
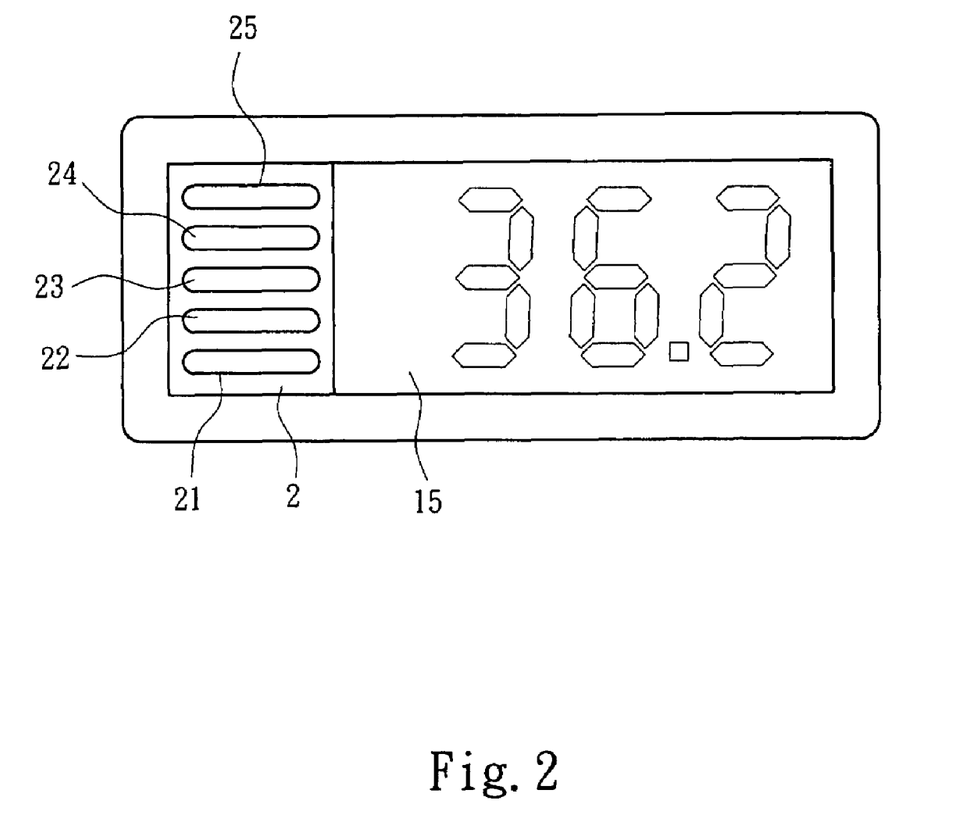
FIG. 2 is a schematic view of an embodiment of the invention.
Figure 3A:
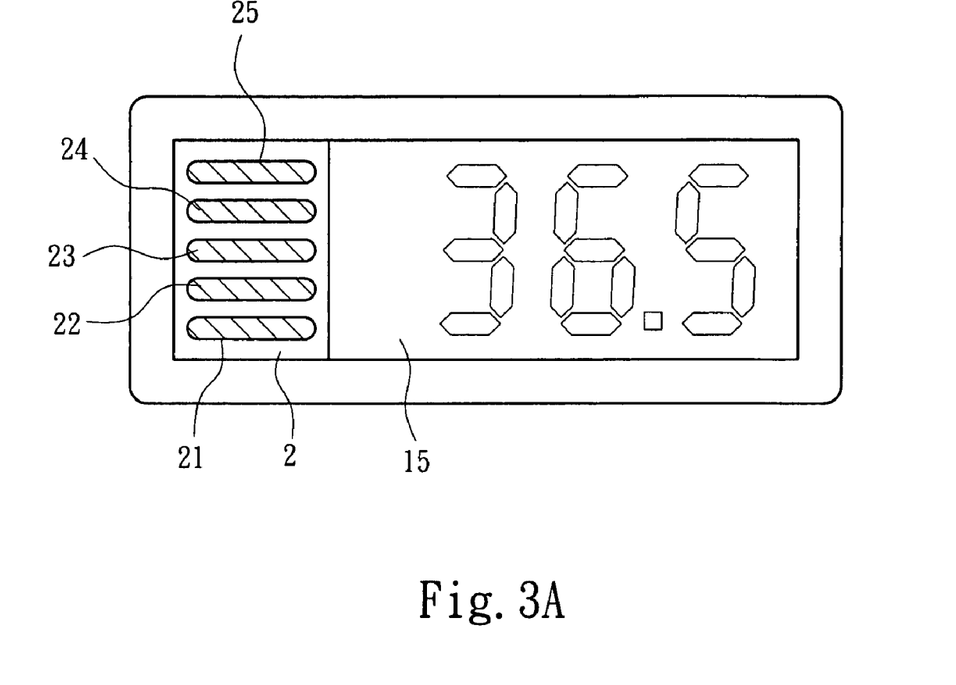
FIG. 3A is a schematic view-A of the invention in an operating condition.
Figure 3B:
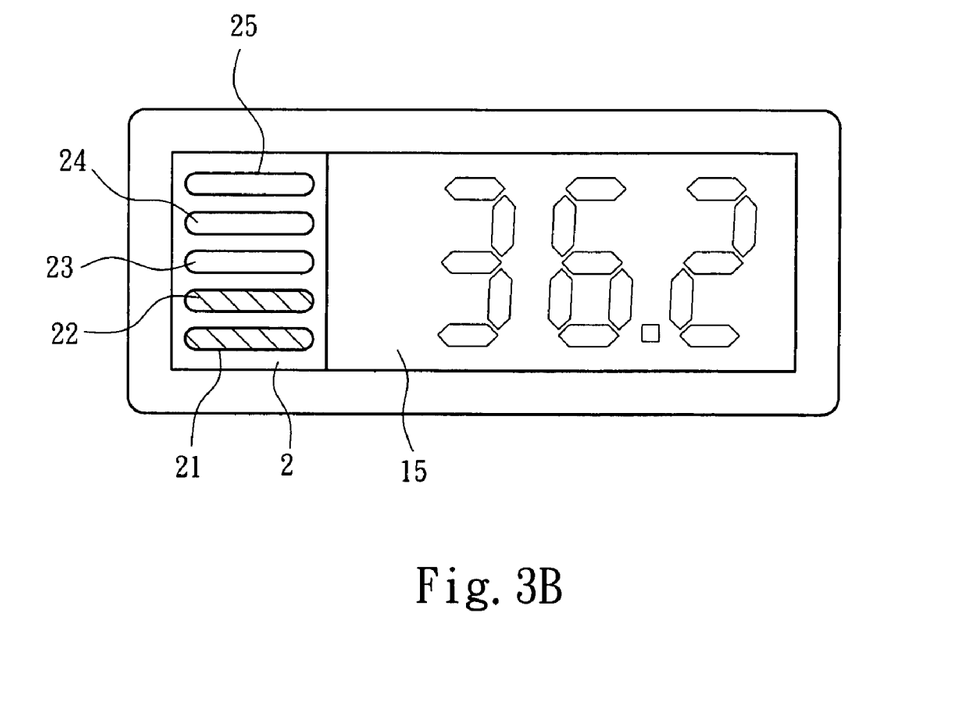
FIG. 3B is a schematic view-B of the invention in an operating condition
Figure 4A:
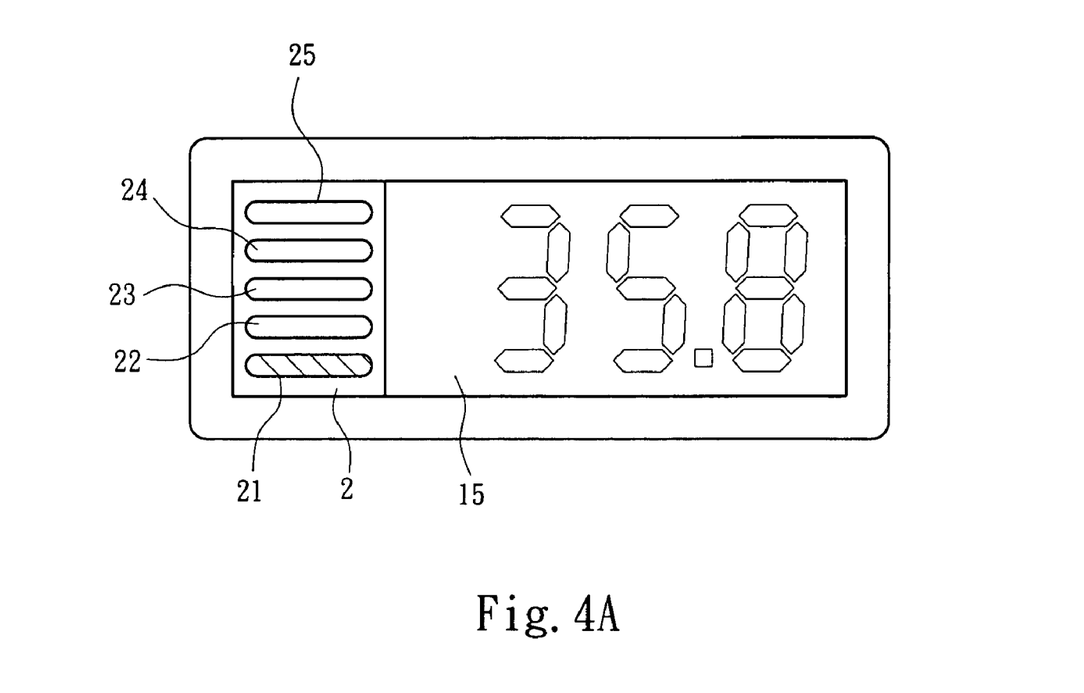
FIG. 4A is a schematic view-A of the invention in another use condition.
Figure 4B:
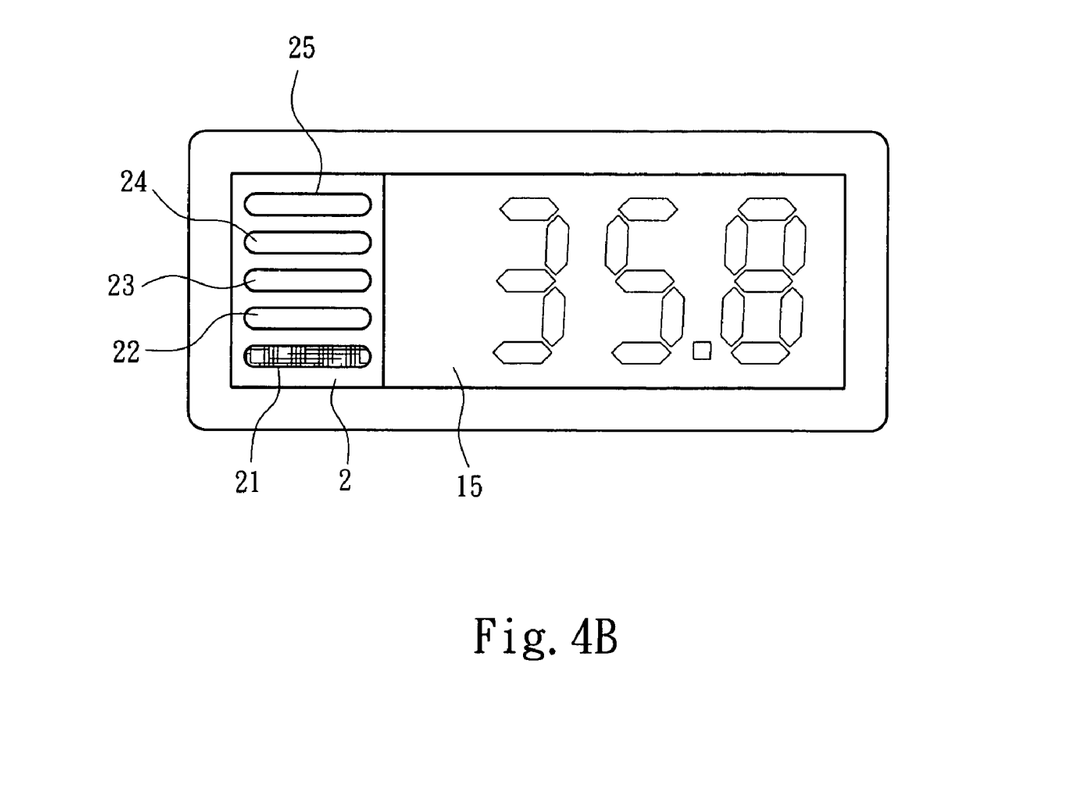
FIG. 4B is a schematic view-B of the invention in another use condition.
Figure 4C:
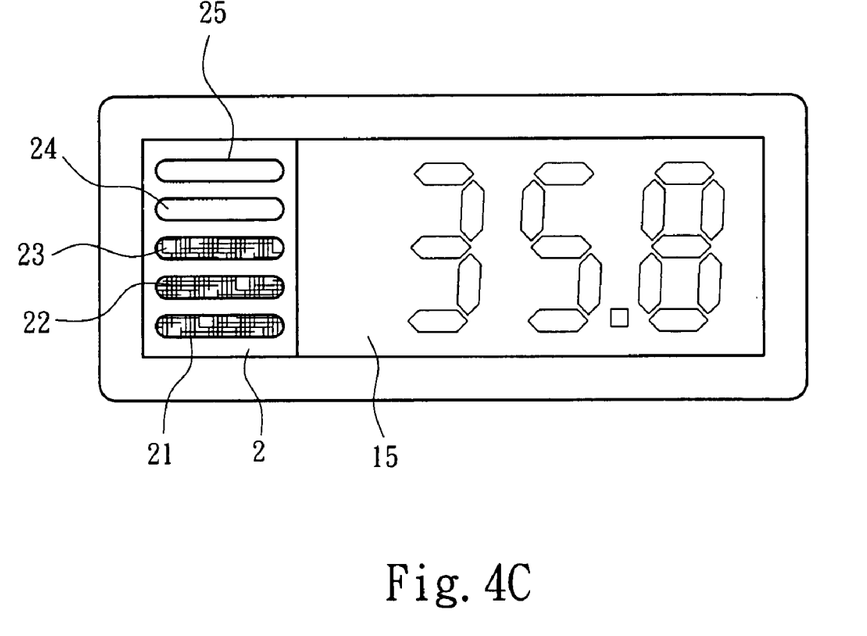
FIG. 4C is a schematic view-C of the invention in another use condition.
Figure 5:
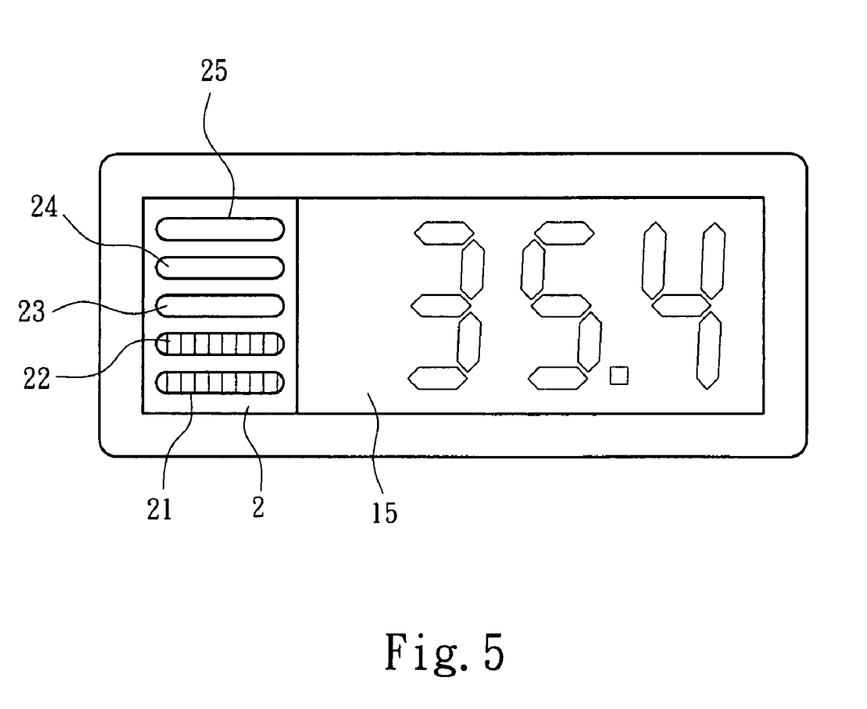
FIG. 5 is a schematic view of the invention in another use condition
Figure 6:
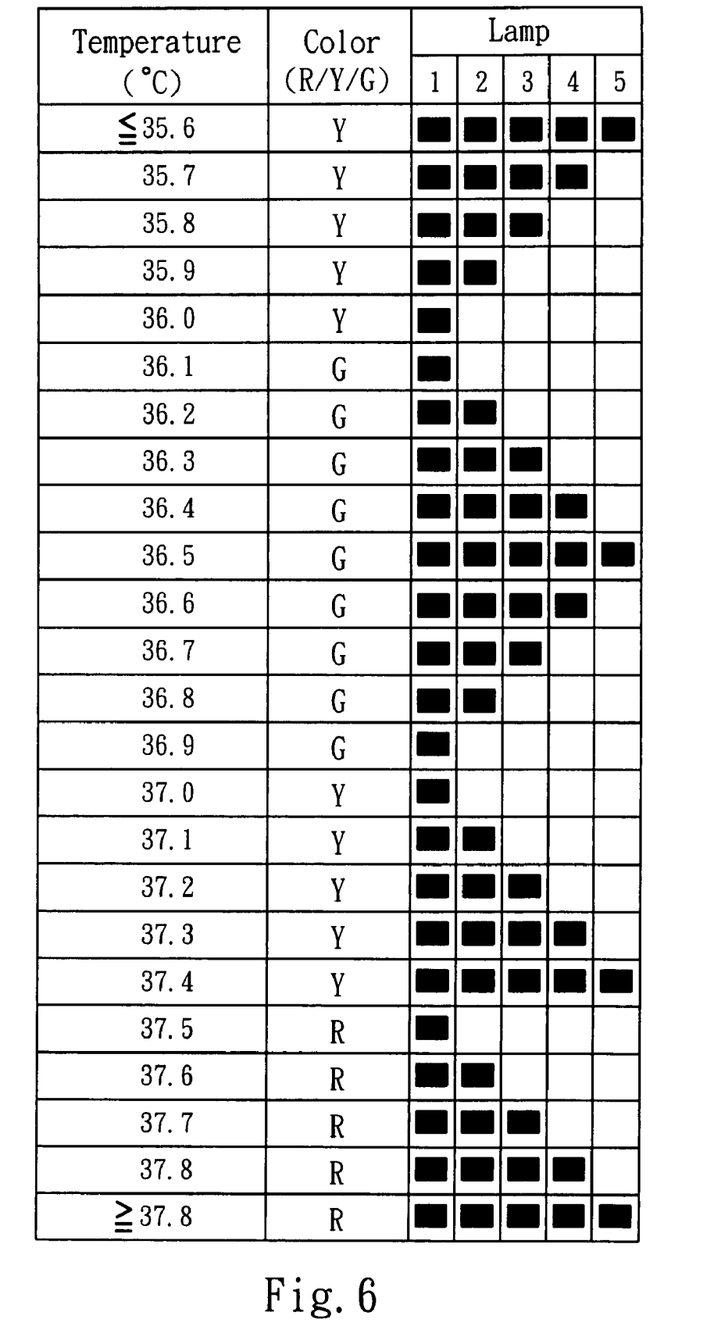
FIG. 6 is a table showing an example of operation sequence according to the invention.

Referring to FIG. 2, after the measured digital value has been processed in the processing unit 12, the digital display device 15 displays the result. The processing unit 12 also sets a plurality of digital segments and a base segment, and determines the segment number between the measured digital value segment and the base segment. The measurement indication apparatus 2 has a plurality of indication lamps to emit three or more colored lights. The light source of the indication lamps may be a LED (light emitting diode). When the measured digital value is within the base segment, all the indication lamps emit light of the first indication color. The number of the indication lamps being turned on decreases gradually according to the interval segment number of the measured digital value segment and the base segment. In the event that the interval segment number between the digital value segment of the measured digital value segment and the base segment is greater than the number of the indication lamps, and the number of the indication lamps lighting in the first indication color decreases to only one, the indication lamps are changed to emit the light of the second indication color, and the number of indication lamps being turned on increases sequentially until all the indication lamps have emitted the light of the second color. In the event that all of the indication lamps emitted the light of the second indication color have been turned on and they still cannot fully represent the difference of segment number between the measured digital value segment and the base segment, the indication lamps are changed to emit the third indication color, and turning on the indication lamps increases from one. By means of such color changing and increasing of number, the number and color of the lamps can indicate the difference between the measured digital value and the normal digital value. For instance, assumed FIG. 2 is a measurement indication of a thermometer, and the normal temperature value is 36.5 degrees, and every 0.1 degree is a digital value segment. Assumed that indication lamps A (21), B (22), C (23), D (24) and E (25) can emit light of three colors green, yellow and red. Referring to FIG. 3A, when the measured digital value is 36.5 degrees, all the indication lamps A (21), B (22), C (23), D (24) and E (25) are turned on to emit the green light. The measured digital value is the normal temperature value. Referring to FIG. 3B, if the measured digital value drops to 36.2 degrees, it is distanced from the normal temperature value by three digital segments. The indication lamps C (23), D (24) and E (25) are turned off, only the indication lamps A (21) and B (22) are turned on to emit the green light. Referring to FIGS. 4A, 4B and 4C, if the measured digital value is 35.8 degrees, it is distanced from the normal temperature value by seven digital segments. The operation sequence of the indication lamps A (21), B (22), C (23), D (24) and E (25) are as follow: the indication lamps B (22), C (23), D (24) and E (25) that emit the green light are turned off sequentially (referring to FIG. 4A), the indication lamp A (21) is changed to emit the yellow light (referring to FIG. 4B), and the indication lamps B (22) and C (23) emit the yellow light sequentially (referring to FIG. 4C). Referring to FIG. 5, if the measured digital value is 35.4 degrees, it is distanced from the normal temperature value by eleven digital segments. The operation sequence of the indication lamps A (21), B (22), C (23), D (24) and E (25) are as follow: the indication lamps B (22), C (23), D (24) and E (25) that emit the green light are turned off sequentially; the indication lamp A (21) is changed to emit the yellow light, and the indication lamps B (22), C (23), D (24) and E (25) emit the yellow light sequentially; the indication lamp A (21) is changed again to emit the red light, and the number of the indication lamps to emit the red light increases gradually until the indication lamp B (22) emits the red light. Hence the measured temperature digital value of 35.4 degrees is indicated by lighting two lamps in red color (referring to FIG. 5). Similar practice is applied when the measured digital value is higher than the normal digital value. Detailed examples of the lighting sequence of the indication lamps are shown in FIG. 6. Thus a graphic information can be generated through colors and the number of lighting lamps.

Figure 7:
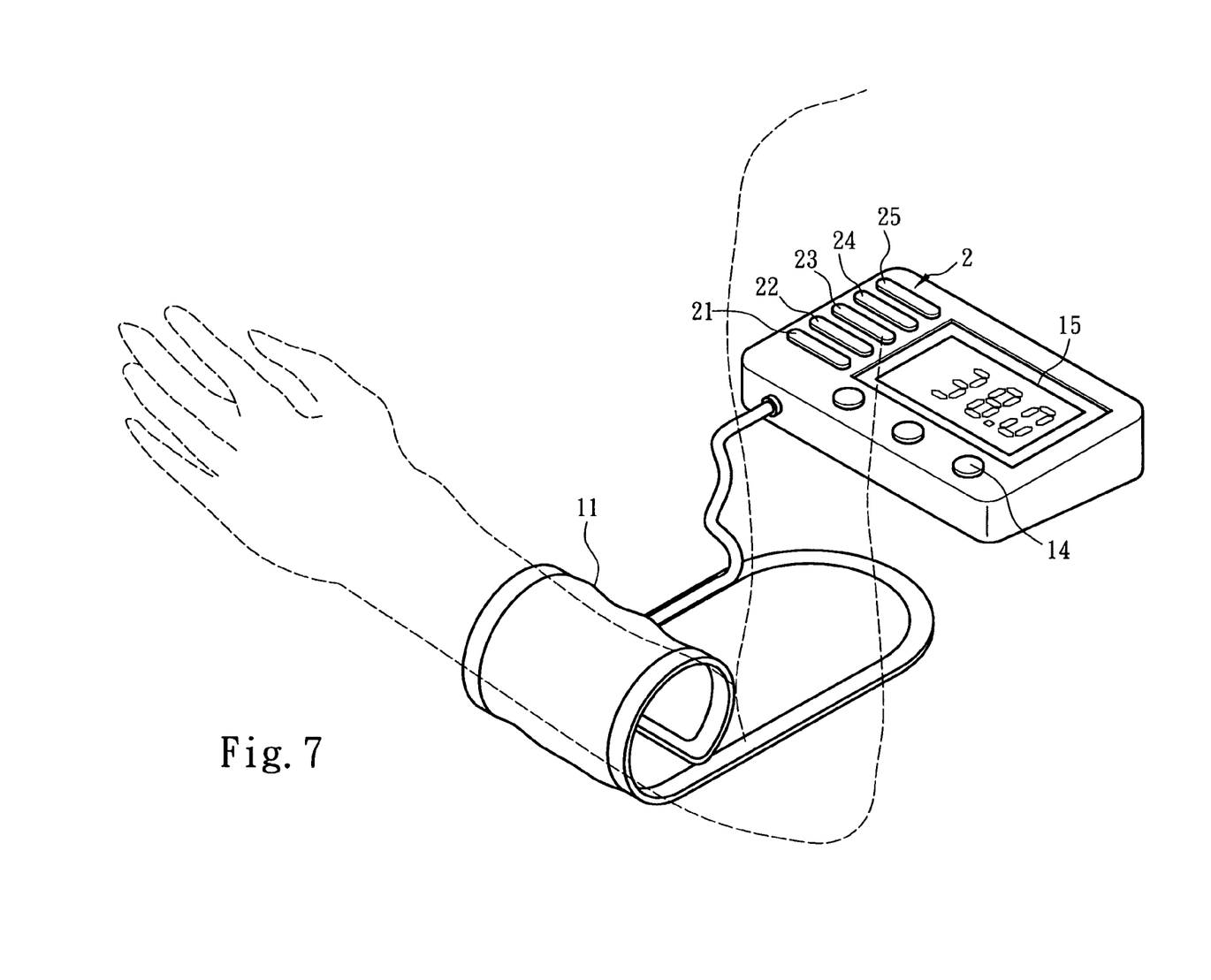
FIG. 7 is a schematic view of an embodiment of the invention.

Refer to FIG. 7 for an embodiment of the invention adopted on a blood pressure meter. Through a user interface 14 or setting of the blood pressure meter, the measurement element 11 can measure the physiological condition of a user. After processed by the processing unit 12, the measured digital value is indicated through the digital display device 15 and the measurement indication apparatus 2. While the digital display device 15 displays the digital value the lighting number and color of the indication lamps of the invention enable the user to quickly understand the difference between the measured digital value and the normal digital value. The colored light of the indication lamps also generates an alert effect to enable users who lack medical knowledge or perception to easily use and interpret the measured result.

There is no limitation on the number and color of the indication lamps of the invention. The final result can be represented by changing the sequence of the lighting lamps or direct displaying. The digital display device 15 of the medical measurement instrument 1 may be a LCD or a CRT display. The invention further may be adapted for use on various medical measurements, such as heart beat and temperature of animals, blood analysis, microbes measurement and the like used in medical research. By merely setting a normal digital value range and a plurality of digital segments, the invention can indicate the difference of the measured result and the normal digital vale range through lighting number and color of the indication lamps. The digital value segments are generated based on the normal digital value which serves as the initial value, and are generated in an equal difference or ratio.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A measurement indication method including setting a base segment and a plurality of digital value segments of equal intervals, getting a measured digital value and controlling a plurality of indication lamps of at least three indication colors to indicate a relative difference of the measured result of a living thing condition and a theoretical digital value, comprising the steps of:
   A. making all of the indication lamps to emit light of a first indication color as an initial condition;
   B. determining the digital value segment of the measured digital value;
   C. calculating segment numbers between the measured digital value segment and the base segment;
   D. turning off sequentially the indication lamps according to the segment numbers between the measured digital value segment and the base segment until only one indication lamp being lighted;
   E. turning on sequentially the indication lamps that are previously turned off to emit light of a second indication color in the event that the number of the indication lamps that were turned off from the first indication color does not reach the segment numbers between the measured digital value segment and the base segment; and
   F. changing the indication lamps to emit light of a third indication color increasing in number from one to indicate the segment numbers between the measured digital value segment and the base segment in the event that the number of the indication lamps that emitted the light of the second indication color still does not reach the segment numbers between the measured digital value segment and the base segment.

2. The method of claim 1 further including an apparatus which has a measurement element, a processing unit, a power supply and an indication lamp set.

3. The method of claim 2, wherein the indication lamp set includes a plurality of indication lamps.

4. The method of claim 3, wherein each of the indication lamps has a light source to emit light of three different colors.

5. The method of claim 2, wherein the apparatus further includes a user interface.

6. The method of claim 2, wherein the apparatus further includes a buzzer alarm.

7. The method of claim 2 wherein the apparatus further includes a digital display device.

8. The method of claim 7, wherein the digital display device is a liquid crystal display (LCD).

9. The method of claim 7, wherein the digital display device is a cathode ray tube (CRT).

10. A measurement indication method including setting a base segment and a plurality of digital value segments of equal intervals, getting a measured digital value and controlling a plurality of indication lamps of at least three indication colors to indicate a relative difference of the measured result of a living thing condition and a theoretical digital value, comprising the steps of:
    A. making all of the indication lamps to emit light of a first indication color as an initial condition;
    B. determining the digital value segment of the measured digital value;
    C. calculating segment numbers between the measured digital value segment and the base segment;
    D. turning off sequentially the indication lamps according to the segment numbers between the measured digital value segment and the base segment until only one indication lamp being lighted;
    E. turning on sequentially the indication lamps that are previously turned off to emit light of a second indication color in the event that the number of the indication lamps that were turned off from the first indication color does not reach the segment numbers between the measured digital value segment and the base segment;
    F. changing the indication lamps to emit light of a third indication color increasing in number from one in the event that the number of the indication lamps that emitted the light of the second indication color still does not reach the segment numbers between the measured digital value segment and the base segment; and
    G. repeating change of the indication color from beginning until the segment numbers between the measured digital value segment and the base segment are represented.

11. The method of claim 10 further including an apparatus which has a measurement element, a processing unit, a power supply and an indication lamp set.

12. The method of claim 11, wherein the indication lamp set includes a plurality of indication lamps.

13. The method of claim 12, wherein each of the indication lamps has a light source to emit light of three different colors.

14. The method of claim 11, wherein the apparatus further includes a user interface.

15. The method of claim 11, wherein the apparatus further includes a buzzer alarm.

16. The method of claim 11, wherein the apparatus further includes a digital display device.

17. The method of claim 16, wherein the digital display device is a liquid crystal display (LCD).

18. The method of claim 16, wherein the digital display device is a cathode ray tube (CRT).

* * * * *